United States Patent
Steffen

(10) Patent No.: US 7,511,480 B2
(45) Date of Patent: Mar. 31, 2009

(54) NON-CONTACT SCANNING USING MAGNETO-RESISTIVE SENSOR

(75) Inventor: Beat Steffen, Saanen (CH)

(73) Assignee: TecPharma Licensing AG, Burgdorf (CH)

( * ) Notice: Subject to any disclaimer, the term of this patent is extended or adjusted under 35 U.S.C. 154(b) by 418 days.

(21) Appl. No.: 11/327,276

(22) Filed: Jan. 6, 2006

(65) Prior Publication Data

US 2006/0161112 A1 Jul. 20, 2006

Related U.S. Application Data

(63) Continuation of application No. PCT/CH2004/000396, filed on Jun. 25, 2004.

(30) Foreign Application Priority Data

Jul. 9, 2003 (DE) ................ 103 30 986

(51) Int. Cl.
- G01B 7/14 (2006.01)
- G01R 33/09 (2006.01)
- H01L 43/08 (2006.01)
- A61M 5/178 (2006.01)

(52) U.S. Cl. .................. 324/207.23; 324/207.21; 604/186

(58) Field of Classification Search .............. 324/207.2, 324/207.21, 207.22, 207.25, 165, 173, 174, 324/178, 179; 604/188, 207, 211
See application file for complete search history.

(56) References Cited

U.S. PATENT DOCUMENTS

| | | | |
|---|---|---|---|
| 4,369,780 A | 1/1983 | Sakai | |
| 4,652,260 A | 3/1987 | Fenton, Jr. et al. | |
| 4,786,870 A | 11/1988 | Kawamata et al. | |
| 4,880,011 A | 11/1989 | Imade et al. | |
| 5,649,810 A | 7/1997 | Schweitzer, Jr. et al. | |
| 5,869,962 A | 2/1999 | Kasumi et al. | |
| 5,998,989 A * | 12/1999 | Lohberg | 324/174 |
| 6,019,745 A | 2/2000 | Gray | |
| 6,456,063 B1 | 9/2002 | Moreno et al. | |
| 7,008,399 B2 * | 3/2006 | Larsen et al. | 604/65 |
| 2002/0143288 A1 | 10/2002 | Larsen et al. | |

FOREIGN PATENT DOCUMENTS

| | | |
|---|---|---|
| DE | 199 07 716 A1 | 8/2000 |
| EP | 0 425 690 A1 | 5/1991 |
| EP | 1 095 668 A1 | 5/2000 |
| FR | 2 600 258 | 12/1987 |
| JP | 63-1345 | 1/1988 |
| WO | WO 02/064196 A1 | 8/2002 |

* cited by examiner

Primary Examiner—Kenneth J Whittington
(74) Attorney, Agent, or Firm—David E. Bruhn; Dorsey & Whitney LLP

(57) ABSTRACT

A device for administering a fluid product includes a measuring assembly for measuring a position between spaced apart elements of the apparatus that can be moved relative to each other. The measuring assembly includes at least one magneto-resistive sensor that is fixed to a first element, such as a casing, and is arranged opposite at least a second element, such as a sleeve, which can be moved relative to the first element. A magnetic device co-operates with the at least one sensor and is formed by a permanent magnet on the first element and a magnetized second element including a magnetic surface profile or including of a number of alternately arranged, different magnetic pole areas.

20 Claims, 3 Drawing Sheets

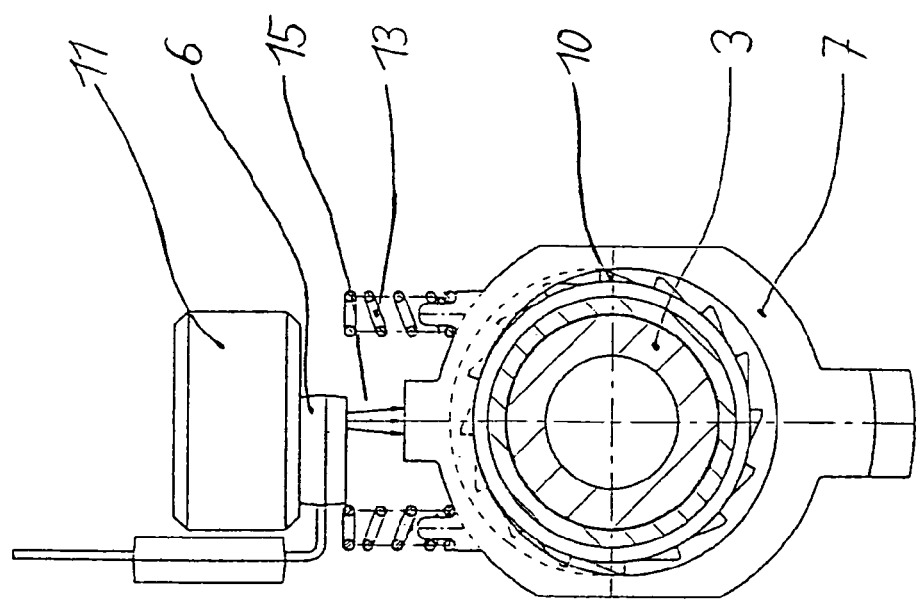
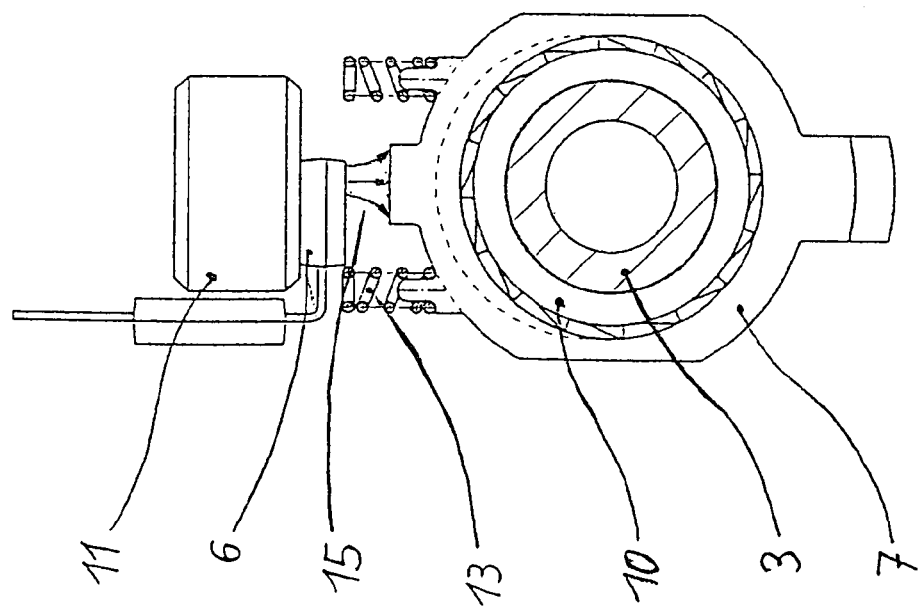
Fig. 3 b
Fig. 3 a

NON-CONTACT SCANNING USING MAGNETO-RESISTIVE SENSOR

CROSS-REFERENCE TO RELATED APPLICATION(S)

This application is a continuation of International Application No. PCT/CH2004/000396, filed on Jun. 25, 2004, which claims priority to German Application No. DE 103 30 986.1, filed Jul. 9, 2003, the contents of both applications are incorporated by their entirety herein.

FIELD OF INVENTION

The present invention relates to a device for administering a fluid, and in particular an injection apparatus comprising a contactless measuring assembly for measuring a position between spaced apart elements that can be moved relative to each other within the administering device. The present invention further relates to a method for measuring an administered substance in this manner.

BACKGROUND

Injection devices are used in broad areas of medicine for administering a medical or pharmaceutical fluid product. Injection apparatuses, such as injection pens, may be used for dispensing insulin, hormone preparations and the like. An injection apparatus comprises various mechanical means, such as an administering or dosing means, in order to precisely dispense a particular product dosage from the apparatus. To monitor the administering process and its accuracy, sensors or probes may be arranged within the apparatus to detect movement of various elements of the mechanical means. From these sensors, the setting of the mechanical means may be measured ascertained, for example, by a microprocessor and may be indicated on the injection apparatus by a mechanical or electronic display.

Because mechanical measurements are susceptible to contamination, moisture and wear, and exhibit large tolerances between the various apparatus components, which affects the accuracy of measurements, non-contact methods for ascertaining settings have been developed. To this end, a number of sensors and measuring devices are arranged at various locations on the apparatus that are suitable for measuring the desired setting without the measured elements coming into contact with the measuring devices or sensors.

An electronic medical administering pen is described in EP 1095668 A1, which measures settings of the administering means by determining the linear position of a helical rod of the administering mechanism or the rotational position of a setting button of a dosing means. To this end, an optical code converter comprising a code disc coupled to the rotational movement of the setting button is provided. The rotational movement of the code disc is measured by an optical receiver. A microprocessor converts the number of rotations by the code disc into a dosage amount corresponding to the setting. Another sensor is provided between the windings of the helical rod of the administering means and registers the movement in the longitudinal direction along the longitudinal axis of the pen. The administered amount of a product is determined from the shift of the helical rod. The two sensors operate independently of each other and determine only one movement direction of a mechanical means of the pen each.

While such contactless measuring means can increase the accuracy in measuring a setting as compared to mechanical scanning, the arrangement of the individual parts of such a measuring means within the apparatus is often complex, such that manufacturing the apparatus is difficult and expensive. In addition, the circuitry of these measuring means are susceptible to moisture, vibrations and other such effects. Accommodating the individual parts of the measuring means, such as the sensors and the counter pieces for the sensors, often requires structural changes in the injection apparatus, making it unnecessarily large or even restricting the other mechanical operations of the apparatus.

Another injection apparatus, which is described in WO 02/064196 A1, is controlled by a closed switch unit comprising integrated sensors that monitor selected parameters of the apparatus. The closed switch unit is fixedly arranged within the injection apparatus. At least two pairs of integrated Hall elements are used as the sensors. The Hall elements cooperate with a magnetised ring that alternately exhibits north and south poles. The ring is arranged within a dosing means and is moved around the longitudinal axis of the injection apparatus in accordance with a rotational movement for setting a product dosage. In order to measure the volume of a dosage setting, it is necessary to determine the rotational movement of the magnetic ring relative to the closed switch unit. To this end, the Hall elements are circularly arranged and are opposing the magnetic ring, in a defined arrangement with respect to each other and the magnetic ring. When movement is started, a start angle is defined and, an end angle is determined once the movement is terminated, based on measurements of the magnetic field during the movement of the magnetic ring relative to the Hall elements. The start and end angles and the measured magnetic field are compared with a stored table and a product dosage set is determined from the comparison.

SUMMARY

The present invention provides a device for administering a fluid and comprises a contactless measuring means for measuring a position between space apart elements that can be moved relative to each other, and a method for such contactless measuring. The administering device exhibits a simple construction, and the measuring means requires few individual parts for measuring. Furthermore, the device provides for a high level of accuracy and reliability and reduces susceptibility to faults and manufacturing costs.

In one embodiment, the present invention comprises a measuring assembly for measuring a position between spaced apart elements of an apparatus, such as an injection or infusion device, that can be moved relative to each other. The measuring assembly includes at least one magneto-resistive sensor that is fixed to a first element, such as a casing, and is arranged opposite at least a second element, such as a sleeve, which can be moved relative to said first element. A magnetic device co-operates with the at least one sensor and is formed by a permanent magnet on the first element and a magnetized second element including a magnetic surface profile or including of a number of alternately arranged, different magnetic pole areas.

An injection apparatus of the present invention may comprise various mechanical components such as an administering or dosing component constructed from a number of elements that are moveable relative to each other within the apparatus when the apparatus is operated. In order to administer a fluid from the device, a sliding element such as a toothed sleeve is moved along the longitudinal axis of the device relative to device casing. A dosing component for setting a dosage volume for a fluid to be administered may include a rotational element that is rotated relative to the casing or a threaded rod. In accordance with the present invention, the injection device further comprises a measuring assembly that measures the movement of the casing and sleeve relative to each other.

The measuring assembly includes at least one magneto-resistive sensor and at least one magnetic device. The magneto-resistive sensor is fixed to a first element of the injection apparatus, such as the casing, and opposes a second element, such as the sleeve, which can be moved relative to the first element. The first element may be the casing of the injection device or an element that is fixed to the casing. The second element, which may be a sleeve, is a sliding or rotational element that is moveable relative to the casing or the element fixed to the casing.

By using magneto-resistive sensors in the injection device, the output measurement signal of the sensors is not dependent on the speed of movement of the elements with respect to each other and provides a reliable measurement signal even when the movement speeds are very low because a frequency of almost 0 Hz can be detected. With a signal amplitude of approximately 20 mV/kA/m, magneto-resistive sensors have a substantially stronger output than Hall-effect sensors; the former's sensitivity is 10 to 100 times stronger, whereas Hall-effect sensors typically have a signal amplitude of only 0.4 mV/kA/m. Accordingly, the magneto-resistive sensors allow for a larger intermediate space between the measuring sensor and the measured element, such that the possible arrangements within the injection device are increased. Furthermore, more cost-effective magnetic devices such as simple rod magnets or magnetic strips may be used. Due to their high mechanical stability, magneto-resistive sensors are also easy to handle, are largely insusceptible to faults, and can be universally employed.

Magneto-resistive sensors utilize the magneto-resistive effect by which a conducting magnetic material in the presence of a variable external magnetic field changes its resistance in accordance with changes in the magnetic field. In order to change a magnetic field applied to the magneto-resistive sensor, the present invention provides for two different types of a magnetic devices that can be employed, individually or coupled together, in an injection apparatus. In both cases, the change in the magnetic field at the sensor is generated by the movement of the opposing elements in the injection apparatus.

In accordance with the present invention, a first type of a magnetic device is formed by a permanent magnet on the first element, such as the device casing, together with at least a second element, such as a moveable sleeve, which can be magnetized and exhibits a predetermined surface profile. The permanent magnet may be a simple bipolar magnet. The permanent magnet is may be arranged on the sensor between the first element and the second element, between the sensor and the second element. The second element may be formed from a paramagnetic material, i.e. a material having a magnetic susceptibility greater than 1. Accordingly, the second element may be formed from a ferromagnetic material such as iron, cobalt, nickel or gadolinium, because a ferromagnetic material has a magnetic susceptibility that is substantially greater than 1. The presence of the permanent magnet of the first element aligns the dipole moments of the ferromagnetic material of the second element in the direction of the magnetic field of the permanent magnet.

The effective magnetic field acting on the sensor arranged on the first element is composed of the magnetic field of the permanent magnet and the magnetic field of the ferromagnetic second element. The magnetisation of the ferromagnetic second element, or its effect on the effective magnetic field, depends on the distance between the surface of the second element and the permanent magnet. In order to generate a change in the magnetic field and therefore a change in the resistance on the sensor, the second element is formed in accordance with the invention with a predetermined surface profile which may be composed of two different height levels which periodically alternate. The predetermined surface profile may be formed by steps or teeth on the surface of the second element. The predetermined surface profile of the second element is arranged opposite the sensor and the magnet of the first element. When the first element and the second element are moved relative to each other, the distance between the sensor or permanent magnet and the surface of the ferromagnetic second element therefore changes periodically, such that the effective magnetic field acting on the sensor likewise changes periodically. This change in the magnetic field in turn generates a change in the resistance in the sensor, which can be measured and outputted as a measurement signal. The distances between the different height levels of the surface profile can be selected in accordance with a desired change in resistance, wherein for example a period of the change in resistance can be defined as a unit of path length travelled. The total path distance travelled during movement can be determined by summing the complete or started units of path length registered by the sensor. It is therefore possible to establish whether a dosage has been completely or only partially delivered, i.e. the entire administering path has not been travelled.

In accordance with the present invention, the predetermined surface profile of the second element may have a variety of shapes or magnetic polarity arrangements. In one embodiment, the surface profile is formed from a toothed rod of an administering means or a toothed wheel of a dosing means. The sensor can then be arranged on a suitable element opposing the toothed rod or toothed wheel.

In another embodiment, the surface profile arranged on the second element is formed by at least one permanent magnet consisting of a number of alternately arranged magnetic pole areas. This results in a vectorial, sinusoidal magnetic field. The distance and size of the magnetic pole areas can be varied. In this way, it is possible to affect the strength and trajectory of the magnetic field and therefore the output signal strength of the sensor. Such a permanent magnet may be formed as a magnetic strip or ring. The magnetic strip or ring is attached to the second element such that it opposes the sensor on the first element, wherein the distance between the sensor and the magnetic strip or ring is selected such that the generated magnetic field generates a change in resistance on the sensor which can be measured. By using a magneto-resistive sensor, this distance can be varied over a broad range and measure up to several millimetres. With this type of the magnetic device, the second element can consist of any material which does not substantially restrict the magnetic field of the permanent magnet.

If the two elements of the injection apparatus are moved relative to each other, as for example when setting a dosage or administering a product, the sensor registers the sinusoidal oscillations in the magnetic field as a change in resistance, wherein the distance between a maximum and a minimum of the magnetic field corresponds for example to a unit of path length travelled. By summing the measured units of path length, the path distance travelled may be determined.

Thus, in a method in accordance with the invention for measuring a position between spaced apart elements of an administering device as described above, a generated change in resistance can be measured at the magneto-resistive sensor when the first element is moved relative to the second element. The change in resistance may occur by altering a magnetic field of a permanent magnet arranged on the first element, thereby changing the distance between the permanent magnet and a surface of at least a second element which can be magnetised, when the elements are moved relative to each other. The change in resistance can also be generated by at least one permanent magnet on at least a second element, consisting of a number of different magnetic pole areas arranged alternately in the movement direction. Both ways of generating the change in resistance on the sensor can be employed, individually or together, in the method. The path distance travelled during movement is detected on the basis of the change in resistance, as previously described. In order to ascertain the position of the movable elements with respect to each other, the path distance travelled is correlated with a reference position of the administering device. To this end, the output measurement signal of the sensor can for example be outputted to a microprocessor which retrieves a value of a reference position, for example from a memory, and determines the new position. An initial position of the elements before starting to move relative to each other serves for example as the reference position. It is also possible to provide a number of measuring units, consisting of a magneto-resistive sensor and a magnetic device in accordance with the invention, in an administering device, in order to determine many different settings of the device or to process the individual measurement signals together. By determining the position of the movable elements of a mechanical means of the administering device, it is possible for example to determine the dosage setting of a fluid product to be administered or the administering path travelled during administering. Accordingly, the dosage actually administered can be detected, which in certain circumstances may differ from a selected, pre-set dosage. It is thus possible to establish whether a dosage has been completely or only partially administered.

With the aid of the invention, it is also possible to indicate the setting of an administering device, such as an injection apparatus, by means of discrete setting positions. The discrete setting positions are for example provided by the period of the change in resistance in the magneto-resistive sensor or by the positions determined by a path distance travelled which consists of a whole multiple of a unit of path length. The periodic change in resistance is then generated, as described above, by a magnetic device in accordance with the invention and by the movement of the elements relative to each other, wherein it is possible to provide reference measurement points, for example by the surface profile comprising at least one reference height level that differs from the periodically alternating height levels or by providing a reference pole area on a magnetic strip or ring in addition to the different magnetic pole areas, said reference pole area differing from the magnetic pole areas for example in the strength of its magnetisation. Using such a reference point, the otherwise periodic change in resistance on the sensor exhibits for example a particularly distinct amplitude which can define a particular setting of the injection apparatus such as a start or end point.

In one embodiment, an injection pen in accordance with the present invention includes a sensor on a first fixed element, opposite both a sliding element and a rotational element. The sensor may be arranged opposite a toothed rod of an administering means and a toothed wheel of a dosing means, such that both the dosage setting and the administering setting of an injection pen can be determined using only one magneto-resistive sensor. In this embodiment, a particularly small number of components are necessary for a measuring means in accordance with the invention for determining the setting of the injection pen.

Discrete rotational positions of the dosing means are then utilized such that for each discrete dosing setting, a row of teeth oppose the sensor along the toothed rod. If the dosing component assumes such a rotational position, the path length travelled by the toothed rod can be measured when the dosage set is administered. The measuring assembly can then measure the path actually travelled by the toothed rod and therefore the volume of a product actually delivered. If, for a dosage set, the complete dosage path length is not transcended, this can lead to under-dosing. Such under-dosing can be registered by measuring the setting in accordance with the invention and reported back to a user.

It is possible to measure a rotational movement and a longitudinal movement of the elements relative to each other using a magnetic device according to the second type of the invention. If a plurality of permanent magnets in the form of magnetic strips or rings are arranged on the second element, these magnetic strips or rings are likewise provided at discrete setting positions of a longitudinal or rotational position, such that proceeding from this discrete position, another movement along these magnetic strips or rings can also be measured.

It is also possible in accordance with the present invention to detect the movement direction within a movement dimension of a moved element, i.e. whether the element is moved forwards or backwards in this dimension. To this end, a characteristic periodicity of the magnetic field of a magnetic strip or ring or of the predetermined surface profile or change in resistance can be determined. If the trajectory of the change in resistance exhibits maxima having one steep and one flat flank, the movement direction can be determined from the sequence of the steep and flat flanks. It is also possible to ascertain the direction with the aid of magnetic fields in which maxima having different heights are formed. It is further possible, in order to measure the movement direction, to provide two different sensors, the measurement signals of which are processed together, wherein their changes in resistance are correlated with each other in accordance with a movement direction. It is also possible, by using two sensors, to establish whether an element is moving along or around the longitudinal axis, or radially with respect to the longitudinal axis of the injection apparatus.

Lastly, it is possible using the present invention to determine the position of elements moving in the radial direction of the longitudinal axis of an injection apparatus. For example, the position of a locking means of an injection apparatus may be measured. Then, it can be determined whether a toothed rod of an administering device has been completely advanced in accordance with a dosage set, until it has reached a locking position. To this end, a magneto-resistive sensor may be attached to a first element that is fixed to the casing and opposes a second element such that the second element can be moved towards and away from the sensor, radially with respect to the longitudinal axis of the injection apparatus. It is not necessary to guide the sensor along the surface of the second element. Such a second element may be a locking element which in a first radial position unlocks the injection apparatus and in a second radial position locks the injection apparatus. The unlocking element may be made of a ferromagnetic material. When the locking element moves radially relative to the sensor, the distance between the sensor and the surface of the locking element is altered. As described above, the magnetic field of a permanent magnet arranged on the sensor is thereby altered and generates a change in resistance in the sensor, from which the position of the unlocking element can be ascertained.

Using a magneto-resistive sensor in accordance with the invention and a magnetic device in accordance with the invention opens up a multitude of ways of constructing a measuring means for an administering device, without foregoing reliable and exact measuring. In particular, it is possible to use the available components of an apparatus for measuring, and to arrange a magneto-resistive sensor at a point within the administering device which is particularly suitable for measuring.

BRIEF DESCRIPTION OF THE DRAWINGS

FIGS. 3a and 3b are cross-section views through a locking means of an injection apparatus in accordance with one embodiment of the present invention.

DETAILED DESCRIPTION OF THE DRAWINGS

With regard to fastening, mounting, attaching or connecting the components of embodiments of the present invention, unless specifically described as otherwise, conventional fasteners such as screws, rivets, toggles, pins and the like may be used. Other fastening or attachment means appropriate for connecting components include friction fitting, adhesives, welding and soldering, the latter particularly with regard to electrical or processing components or systems. Any suitable electronic, electrical, magnetic, electromagnetic, communication, control or controller, computer or processing components may be used, including any suitable electrical components and circuitry, wires, wireless components, sensors, chips, boards, micro-processing or control system components, software, firmware, hardware, etc.

Figure 1:
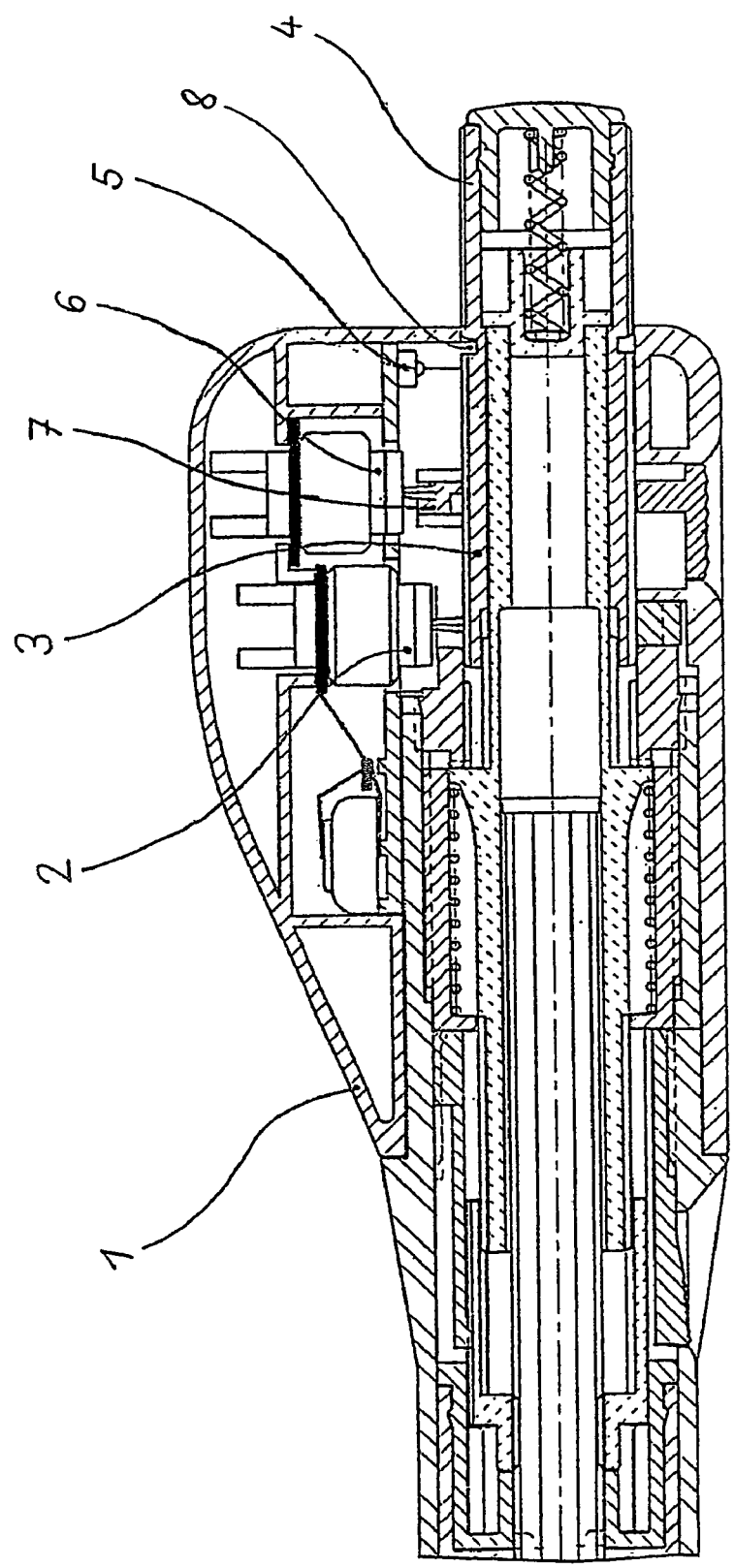
FIG. 1 is a longitudinal cross-section view through a rear area of an injection device in accordance with one embodiment of the present invention.

FIG. 1 shows the rear area of an injection device comprising the substantial parts of a dosing and an administering means in accordance with one embodiment of the present invention. The individual elements are accommodated within a casing 1. A first magneto-resistive sensor 2 is fixedly connected to the casing 1 within the injection apparatus, such that the casing 1 represents a first element in the sense of the invention. The magneto-resistive sensor 2 is arranged opposite a sleeve 3 which can be rotated around the longitudinal axis of the injection apparatus and shifted along the longitudinal axis, relative to the casing 1. Sleeve 3 represents a second element which can be moved relative to the first element, wherein the sleeve 3 serves both as a rotational element of the dosing means for setting a product dosage to be administered and as a sliding element for advancing a piston within a product reservoir (not shown). In order to administer a product, the sleeve is first rotated at its end 4 protruding out of the injection apparatus, in accordance with a desired dosage, and then advanced by pressing the end 4 into the injection apparatus.

A light barrier 5 is likewise arranged opposite the sleeve 3. The light barrier 5, in conjunction with the magneto-resistive sensor 2, serves to determine the movement direction of the sleeve 3, i.e. whether the sleeve is being moved in the circumferential direction or in the longitudinal direction relative to the casing 1. Light barrier 5 may be formed from conventional energy-saving components. In another embodiment, the movement direction may be established by arranging switches, such as Reed contacts or mechanical switches, in the device.

A second magneto-resistive sensor 6 is fixedly connected to the casing 1. The second sensor 6 is arranged opposite a movable element 7 of a locking means of the injection apparatus. The movable element 7 of the locking means is provided by a reset ring which in its unlocked state enables the sliding element to be advanced and in its locked state prevents such movement. To this end, the reset ring 7 can be shifted in the radial direction with respect to the longitudinal axis of the injection apparatus and engages with a groove 8 on the sleeve 3 in order to lock.

The magneto-resistive sensors may be formed from a variety of known sensors. In one embodiment, the magneto-resistive sensors are Philips' KMI 15/X series sensors. Other magneto-resistive sensors from other manufacturers may also be employed. The first magneto-resistive sensor 2, the second magneto-resistive sensor 6, and the light barrier 5 are connected to a microprocessor which collects and processes the signals from the sensors 2 and 6 and the light barrier 5. The microprocessor is likewise fixed within the casing 1 of the injection apparatus, near the sensors. It is not necessary for the sensors and the microprocessor to be formed as a common, closed component. This enables the sensors to be arranged within the injection apparatus at a point which is particularly suitable for measuring.

Figure 2:
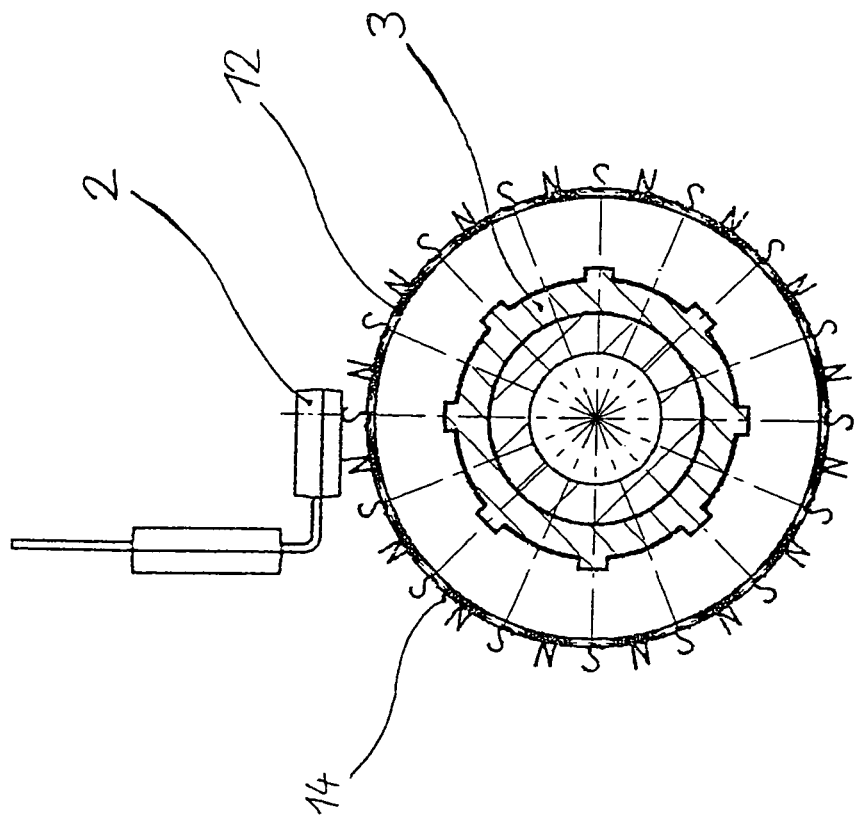
FIGS. 2a and 2b are cross-section views through a rotational element in accordance with one embodiment of the present invention.
Figure 2:
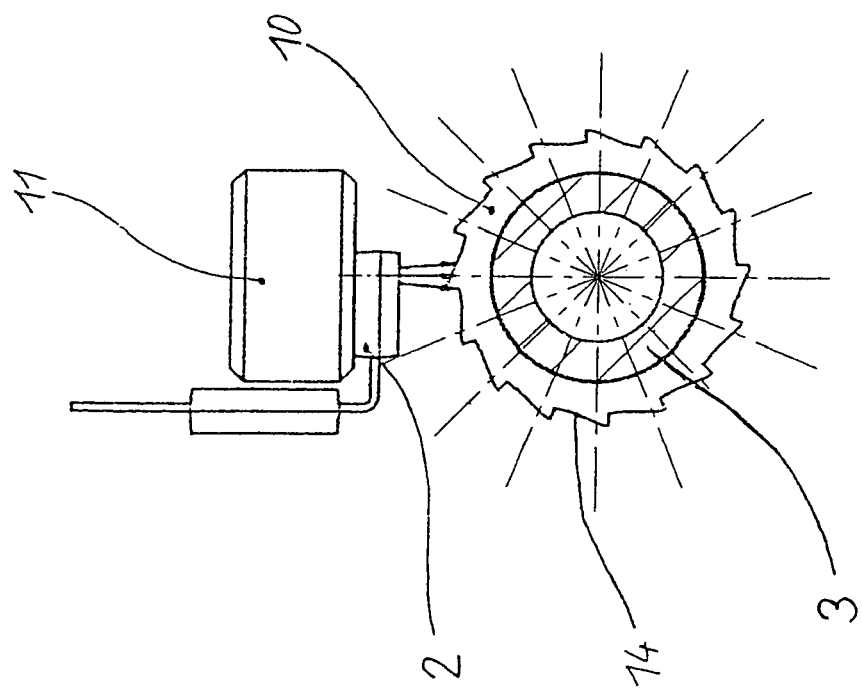

FIG. 2a shows a cross-section through a sleeve 3 exhibiting a predetermined surface profile 14. The surface profile 14 is formed by a toothed wheel 10 on the sleeve 3. The teeth of the surface profile define discrete rotational positions of the sleeve 3 that correspond to a particular dosage amount set. In accordance with particular discrete rotational positions of the sleeve 3, magnetic strips are arranged adjacent to the tooth wheel along the surface of the sleeve 3 in the longitudinal direction of the injection apparatus, said magnetic strips comprising a number of alternately arranged, differently poled magnetic pole areas (not shown in the drawing).

If the sleeve 3 assumes one of the discrete rotational positions and is then advanced into the injection apparatus in the advancing direction, the magnetic strip corresponding to this rotational position is shifted along the sensor, such that the latter can also measure the path distance of the shift, according to the rotational position. Discrete setting positions can also be determined in the longitudinal direction, in accordance with the distance between the different magnetic pole areas on the magnetic strip. As soon as the sleeve 3 is moved in the advancing direction, the light barrier 5 can for example register this longitudinal movement, by the groove 8 being slid past it at the start of advancing.

The first magneto-resistive sensor 2 is arranged above the toothed wheel 10. A permanent magnet 11 is arranged over the magneto-resistive sensor 2. The permanent magnet 11 is therefore also fixed to the first element, the casing 1. The permanent magnet 11 generates, of its own accord, an invariable magnetic field shown in the drawing by arrows in the direction of the toothed wheel 10. The toothed wheel 10 is manufactured from a material which can be magnetized. For instance, the wheel 10 may be formed from a ferromagnetic material such as iron, nickel, cobalt or alloys of these having a susceptibility constant $\mu \gg 1$. The predetermined surface profile 14 of the toothed wheel 10 consists of a number of teeth which are arranged at equal distances and exhibit a steep radial flank on one side and a flatly sloping flank on the other side. This results in a surface profile 14 exhibiting a first height level between the teeth and a second height level at the tips of the teeth. When the toothed wheel 10 is rotated past the sensor by the sleeve 3, the distance between the surface of the toothed wheel 10 and the sensor 2 therefore varies periodically in accordance with these two height levels. The magnetic field of the magnet 11 is deflected differently at different distances between the magnet and the sensor 2 and thus affects the effective magnetic field acting on the sensor, such that a change in resistance arises in the sensor 2. Due to the asymmetric shape of the teeth of the toothed wheel 10, exhibiting one steep and one flat flank, it is also possible to determine the rotational direction of the toothed wheel 10 and therefore of the sleeve 3. By determining the rotational direction, a dosage adjustment can also be identified and correctly performed. For example, the dosage adjustment may be identified by moving the dosing means back.

FIG. 2b shows an alternative embodiment of the sleeve 3. The circumferential face of the sleeve 3 opposing the sensor 2 is provided with a permanent magnetic ring 12 which comprises a number of alternately arranged, different magnetic pole areas, i.e. north and south pole areas, designated by N and S. In this embodiment of the injection apparatus, a permanent magnet 11 is not necessary. Such a magnetic ring 12 can be attached to the sleeve after it has been manufactured. When the sleeve 3 is rotated, the alternating poles of the magnetic ring generate a sinusoidal magnetic field at the sensor 2 and therefore a change in resistance on the sensor 2. The distance between the magnetic pole areas N and S can be selected in accordance with the resolution capacity of the sensor. Conventionally available magneto-resistive sensors enable a sufficiently small distance that even small path lengths or a small radian can be measured. It is therefore possible to measure the setting of the injection apparatus very precisely. It is also possible to select the distances between the magnetic pole areas N and S in accordance with discrete setting positions which are generally larger than the distance which can still be measured by the sensor.

FIG. 3a shows a cross-section through a locking means of the injection apparatus in accordance with the invention, in an unlocked position. The surface of the reset ring 7 is arranged opposite the sensor 6, at a first distance. A permanent magnet 11 is fixed over the magneto-resistive sensor 6 and generates a magnetic field in accordance with the indicated arrows in the direction of the reset ring 7. At the end of an advancing movement by the sleeve 3, the reset ring 7 is pressed into the groove 8 by a spring force from biased springs 13. This advancing movement changes the distance between the surface of the reset ring 7 and the sensor 6 from the first distance to a second, larger distance. The change in the distance between the reset ring 7 and the sensor 6 also changes the field line trajectory of the effective magnetic field 15 acting on the sensor 6, and therefore the resistance within the sensor 6, as shown in FIG. 3b by the vectors of the magnetic field. The locking position of the locking means of the injection apparatus can then be measured. A particular surface profile on the surface of the reset ring 7 is not necessary, since a change in the distance between the first and second element results alone from the movement of the elements relative to each other.

In accordance with the arrangements of sensors and moved elements shown, a multitude of movement trajectories within an administering device can be measured and the setting of the device therefore determined. The arrangement shown is therefore to be understood as an example and is not intended to restrict the scope of the invention.

The invention claimed is:

1. A fluid administration device comprising a measuring assembly for measuring a position between spaced apart elements of said device, said measuring assembly comprising:
   at least one magneto-resistive sensor, said magneto-resistive sensor being fixedly connected to a casing of said device and being arranged opposite a sleeve of said device, said sleeve being rotationally and axially movable relative to said casing and being spaced apart from said casing, said sleeve serving both as a radially rotational dosing element for setting a dose amount to be administered and as an axial sliding element for administering a dose of fluid;
   a first permanent magnet fixedly arranged relative to said casing; and
   at least one second permanent magnet including a predetermined surface profile fixedly attached to said sleeve, said predetermined surface profile configured to enable detection by the at least one magneto-resistive sensor of (a) the set dose amount based upon radial rotation of the sleeve with respect to the casing and (b) the administration of the dose of fluid based upon axial movement of the sleeve with respect to the casing, wherein said magneto-resistive sensor is spaced apart from said surface profile.

2. The fluid administration device as claimed in claim 1, wherein said second permanent magnet includes a plurality of magnetically polarized areas on the surface profile arranged with alternating polarities.

3. The fluid administration device as claimed in claim 2, wherein said first permanent magnet on the casing is a rod magnet.

4. The fluid administration device as claimed in claim 2, wherein said second permanent magnet includes at least one magnetic reference pole area that differs in polarity from the plurality of magnetically polarized areas.

5. The fluid administration device as claimed in claim 2, wherein discrete dose setting positions of the sleeve are determinable based on the alternately arranged magnetic pole areas on the surface profile.

6. The fluid administration device as claimed in claim 1, wherein said first permanent magnet is arranged on the magneto-resistive sensor.

7. The fluid administration device as claimed in claim 1, wherein said second permanent magnet is ferromagnetic.

8. The fluid administration device as claimed in claim 1, wherein said surface profile includes at least two periodically alternating height levels.

9. The fluid administration device as claimed in claim 8, wherein the surface profile comprises at least one reference height level that differs from the periodically alternating height levels.

10. The fluid administration device as claimed in claim 1, wherein said second permanent magnet includes a magnetic strip or ring.

11. The fluid administration device as claimed in claim 1, wherein said at least one second permanent magnet includes a plurality of magnetic strips arranged along the longitudinal axis of the sleeve at circumferential positions thereon.

12. The fluid administration device as claimed in claim 11, wherein said circumferential positions of the plurality of magnetic strips correspond to discrete rotational positions of the sleeve.

13. A method for measuring a position between spaced apart elements of a fluid administration device, comprising the steps of:
   measuring with a magneto-resistive sensor a change in resistance generated between a casing of the fluid administration device and a sleeve of said fluid administration device when the casing and the sleeve are moved relative to each other in a radial direction around a longitudinal axis of the administration device, thereby causing alteration of a magnetic field of a first permanent magnet fixedly arranged relative to said casing wherein the distance between the first permanent magnet and a surface profile of a second permanent magnet fixedly attached to said sleeve is changed;

detecting a first radial movement of the sleeve based on the measured change in resistance to enable detection of a set dose amount; and detecting a second movement of the sleeve along the longitudinal axis of the administration device to enable detection of administration of a dose of fluid.

14. The method as set forth in claim 13, wherein the distance between the surface of the first permanent magnet and the surface profile of the second permanent magnet changes when the elements are moved relative to each other due to height variations in the surface profile.

15. The method as set forth in claim 13, wherein the second permanent magnet is ferromagnetic and is magnetised by the movement of the sleeve and the casing relative to each other.

16. The method as set forth in claim 13, wherein detecting the first movement of the sleeve comprises ascertaining discrete setting positions of the sleeve.

17. The method as set forth in claim 13, further comprising measuring a locking position of a locking means of the administration device.

18. A method for measuring a position between spaced apart elements of a fluid administration device, comprising the steps of:

measuring with a magneto-resistive sensor a change in resistance generated between a casing of the fluid administration device and a sleeve of said fluid administration device when the casing and the sleeve are moved relative to each other around and along a longitudinal axis of the administration device, thereby causing alteration of a magnetic field of a first permanent magnet fixedly arranged relative to said casing, wherein a surface profile of a second permanent magnet fixedly attached to said sleeve includes a plurality of magnetically polarized areas arranged with alternating polarities is moved relative to said first permanent magnet;

detecting a first movement of the sleeve around the longitudinal axis of the administration device based on the magnetic field alteration to enable detection of a set dose amount; and detecting a second movement of the sleeve along the longitudinal axis of the administration device based on the magnetic field alteration to enable detection of administration of a dose of fluid.

19. The method as set forth in claim 18, wherein detecting the first movement of the sleeve comprises ascertaining discrete setting positions of the sleeve.

20. The method as set forth in claim 18, further comprising measuring a locking position of a locking means of the administration device.

* * * * *